United States Patent [19]
Braun et al.

[11] Patent Number: 5,425,754
[45] Date of Patent: Jun. 20, 1995

[54] INFRARED RADIATION LAMP APPARATUS HAVING A CUVETTE POSITIONED IN ITS OPTICAL PATH AND A METHOD FOR USING THE SAME

[75] Inventors: Werner Braun, Wilen-Sarnen; Asim Maner, Kerns, both of Switzerland; Jerry Rzeznik, Heuchelheim, Germany

[73] Assignee: Maxs AG, Sachseln, Switzerland

[21] Appl. No.: 207,740

[22] Filed: Mar. 8, 1994

[30] Foreign Application Priority Data

Mar. 8, 1993 [DE] Germany .................. 9303352 U

[51] Int. Cl.⁶ ............................................. A61N 5/06
[52] U.S. Cl. ............................................. 607/88
[58] Field of Search ......................... 607/88–94

[56] References Cited

FOREIGN PATENT DOCUMENTS 3721937  1/1989  Germany ............................ 607/88

OTHER PUBLICATIONS

WO90/00420; Jan. 1990; Rowland et al.

Primary Examiner—Angela D. Sykes
Attorney, Agent, or Firm—Skjerven, Morrill, MacPherson, Franklin & Friel; Alan H. MacPherson

[57] ABSTRACT

In an infrared radiation lamp, the optical path has provided therein a cuvette which is filled with a liquid containing water and a fungicidal agent. The cuvette consists of two opposite transparent panes and a casing receiving said panes. The liquid inside the cuvette is a buffer solution with a pH of 7, preferably based on phosphate.

7 Claims, 2 Drawing Sheets

INFRARED RADIATION LAMP APPARATUS HAVING A CUVETTE POSITIONED IN ITS OPTICAL PATH AND A METHOD FOR USING THE SAME

The present invention relates to an infrared radiation lamp which serves thermotherapeutical purposes and comprises a hermetically sealed hollow cuvette which is positioned within the optical path and filled with a liquid that preferably contains water and an addition exhibiting a bactericidal and fungicidal effect.

Such a radiation lamp is, e.g., known from EP 311 898. A filter which comprises two transparent plane-parallel panes that are held by a frame and define a closed cavity containing a medium which selectively influences the radiation spectrum and is in contact with at least part of the frame is positioned there at the housing outlet within the optical path between patient and radiation source. Since the filter is considerably heated in the course of the filtering process during operation, a cooling means is most of the time provided on the filter. Such a cooling means may, e.g., be composed of cooling ribs that are mounted on the filter and made from a material of high thermal conductivity, such as aluminum.

The total of the radiation spectrum emitted from the radiation source has, however, side effects and is thus not suited for thermotherapy. It includes spectrum portions that are already greatly absorbed on the skin surface, which means an intolerable heat sensation for a patient. The patient will not accept such a radiation and will break off the treatment prematurely before any therapeutically effective heat dosage can be formed.

These undesired spectrum portions are intercepted by the filled cuvette disposed within the optical path of the radiation lamp and the above-mentioned side effects are thereby eliminated.

Purified water which has the desired spectrum-forming filtering effect is most of the time used as the filtering medium. Normal tap water is not used because the amount of the impurities contained therein varies from time to time.

An additional problem is posed by the bacteria and fungal spores which are often found in tap water and proliferate excessively under the action of heat and grow rapidly, supported by inoperative times. This will impair the filtering efficiency both with a view to the selective behavior and the transparency of the filter, which is bound to reduce the therapeutical effect apart from an overheating of the liquid within the cuvette.

To prevent turbidity of the filter caused by fungi and bacteria, antiseptics and fungicides are normally added to the water to keep the water clear and free from germs. Nevertheless, turbidities cannot be ruled out entirely.

It is therefore the object of the present invention to achieve a constantly high and efficient filtering effect of the water-filled hollow cuvette during operation of the radiation lamp.

This object is attained according to the invention in that the liquid in the cuvette consists of a buffer solution which has a pH of 7 and is preferably based on phosphate. The buffer solution together with the fungicidal agents prevents the liquid from becoming turbid and thus leads to a constantly high filtering effect.

The addition of an NaAgCl complex with an antiseptic and fungicidal effect has been found to be especially advantageous. The formation and propagation of mould fungi and bacteria and the resultant turbidity of the cuvette contents are thereby counteracted. An NaAgCl complex which is sold by Katadyn-Produkte AG in CH-8394 Walliselen/ Switzerland using "Micropur MT 1" may be used.

It is here of special advantage to use a buffer solution based on potassium hydrogen phosphates, which cooperates with the NaAgCl complex in an advantageous manner. A "buffer solution ready for use pH 7 + −0.02 (20° C.)", which is commercially sold by D. Merck in D-6100 Darmstadt under article number 9439.1 and 9439.901, respectively, may be used.

Surprisingly enough, the use of an NaAgCl complex together with the buffer solution does not pose any problems in cuvettes with aluminum casings although it is pointed out in the product specification of "Micropur MT 1" that said agent is suited for aluminum vessels to a limited degree only.

An embodiment of the invention shall now be explained in more detail with reference to a drawing, in which.

Figure 1:
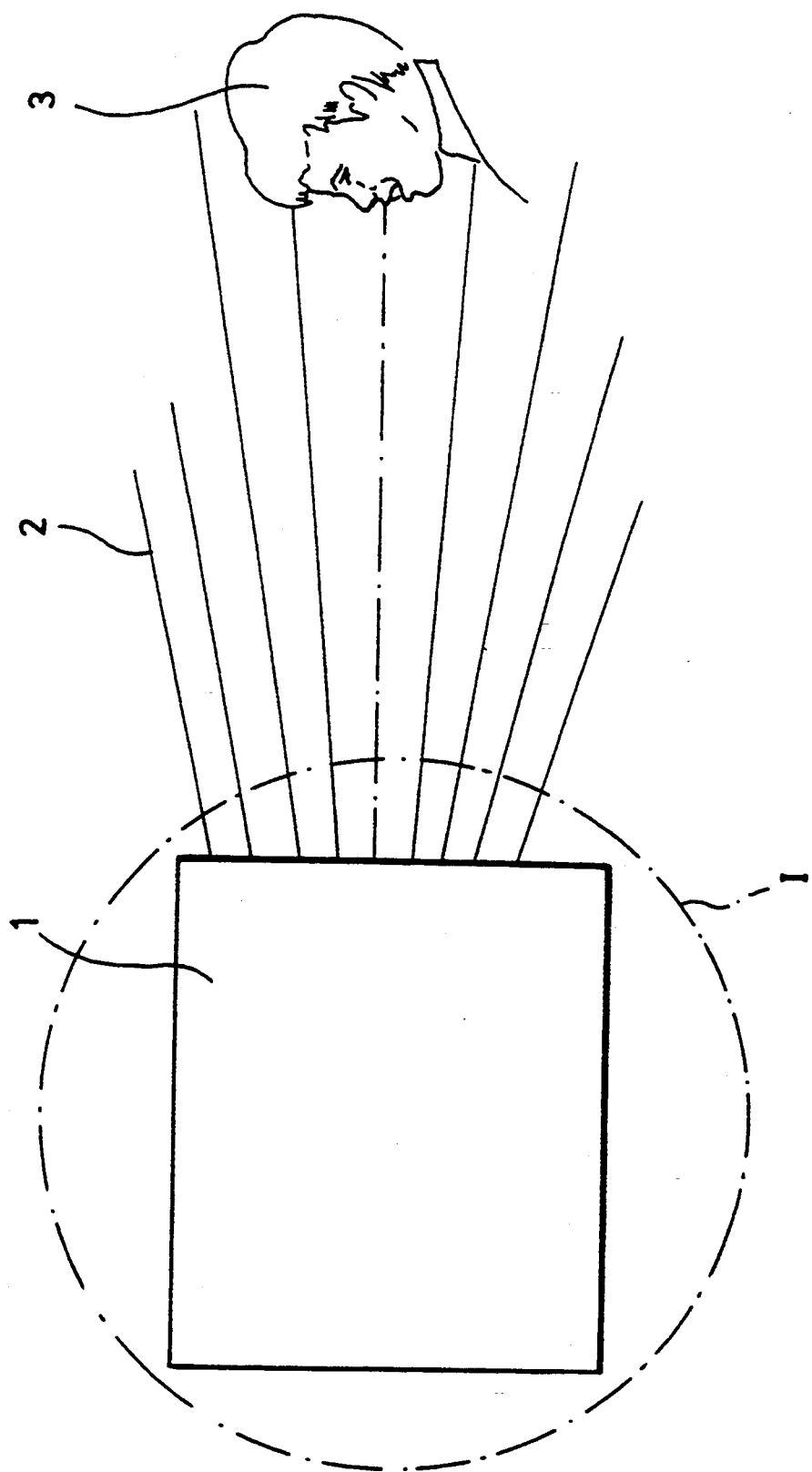
FIG. 1 is a diagrammatic illustration of the assembly with radiation lamp and person to be treated.

FIG. 1 illustrates the whole assembly comprising a radiation lamp 1 which emits rays with an optical path 2. The optical path 2 has positioned therein a person 3 who is to be treated, with the part of person 3 that is to be treated being within the optical path and facing radiation lamp 1. A cuvette 4 is positioned between person 3 and radiation lamp 1 within the optical path 2.

Figure 2:
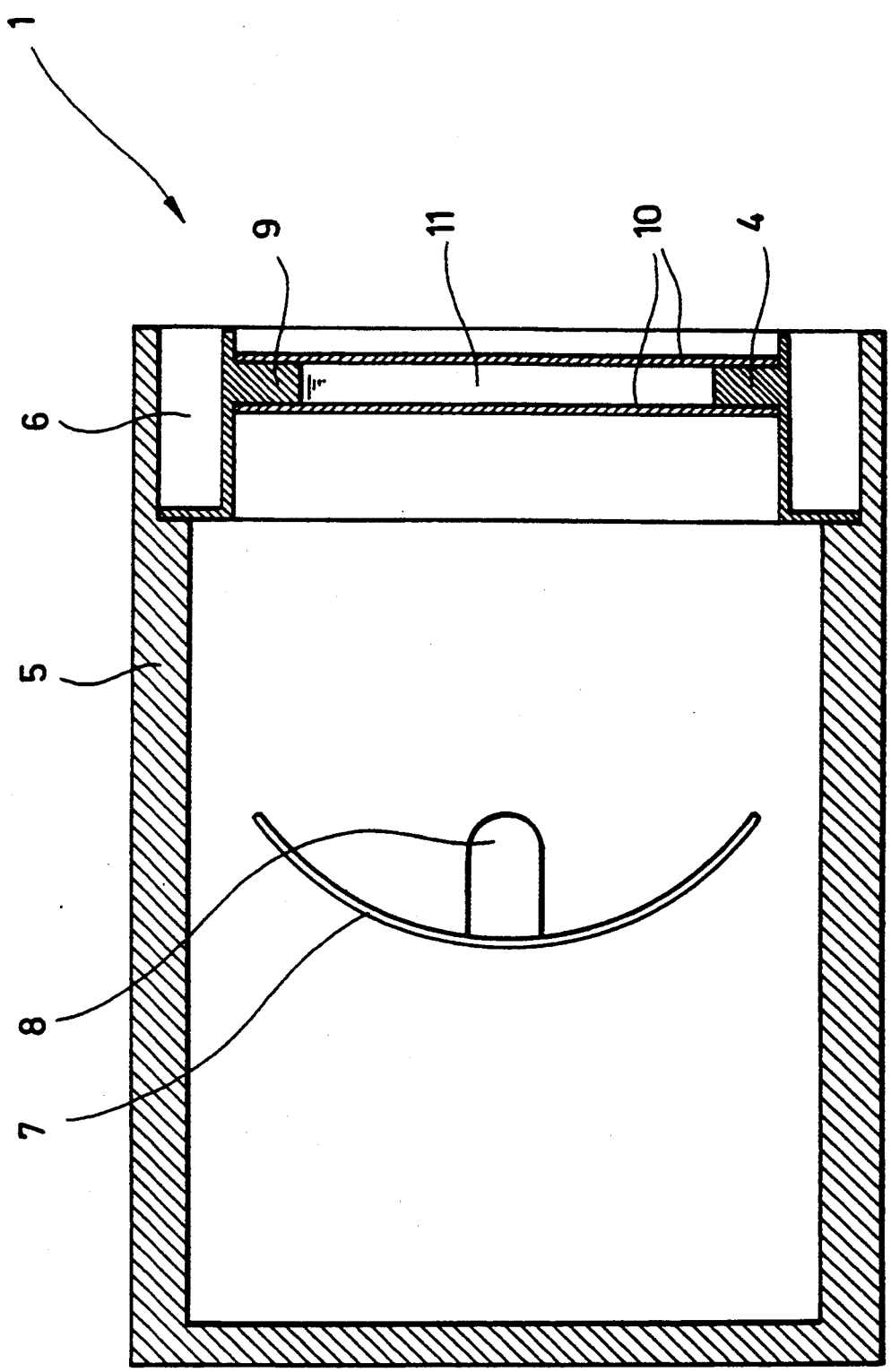
FIG. 2 is a diagrammatic sectional view of the detail of FIG. 1.

FIG. 2 illustrates the radiation lamp 1 with a casing 5 having an opening 6, a reflector 7, a radiation source 8 and cuvette 4.

Cuvette 4 consists of a casing 9 made of aluminum, two plane-parallel transparent boundaries 10 which are normal to the optical path and mounted in a waterproof manner, and neutralizing water 11 within said cuvette, the water having added thereto a neutralizing buffer solution which contains potassium hydrogen phosphate and disodium hydrogen phosphate and is sold by Merck at D-6100 Darmstadt under the name "buffer solution ready for use pH 7.00+ −0.02 (20° C.)" under article number 9439.1 and 9439.9010, respectively. An NaAgCl complex which has an antiseptic and fungicidal effect and is sold by Katadyn Produkte AG at Zicha-8304 Wallisellen/Switzerland under the name "Micropur MT1" is additionally added to the water.

The operation and function of the invention shall now be explained in more detail hereinafter:

The radiation emitted by radiation source 8 is passed by reflector 7 through opening 6 out of casing 5 and impinges upon cuvette 4. In cuvette 4, water 11 which is inside cuvette 4 filters the wavelengths not desired for the treatment out of the radiation emitted from radiation source 8. The remaining radiation subsequently exits from the cuvette and impinges upon the person, with the radiation developing its therapeutical effect.

The NaAgCl complex which has an antiseptic and fungicidal effect and is within water 11 prevents the formation and propagation of bacteria and mould fungi. Any increase in the broadening of the absorption bands is here prevented, which has the side effect that the heat development is reduced to the desired degree.

We claim:

1. An infrared radiation lamp apparatus, comprising:

a cuvette having two opposing transparent panes and a casing receiving the panes, the cuvette containing a liquid, and the cuvette positioned so that infrared light emitted by a lamp is transmitted through the liquid;

wherein the liquid comprises a fungicidal agent in a phosphate buffered solution having a pH of about 7.

2. Apparatus as in claim 1, wherein the fungicidal agent comprises an NaAgCl complex.

3. Apparatus as in claim 1 or 2, wherein the solution comprises a potassium hydrogen phosphate.

4. A method for providing thermotherapy, comprising the steps of:

providing an infrared radiation lamp having a cuvette with two opposing transparent panes and a casing receiving the panes, the cuvette containing a liquid; and transmitting infrared light emitted by the lamp through the liquid;

wherein the liquid comprises a fungicidal agent in a phosphate buffered solution having a pH of about 7.

5. The method of claim 4 wherein the fungicidal agent comprises an NaAgCl complex.

6. The method of claim 4 wherein the solution comprises a potassium hydrogen phosphate.

7. The method of claim 5 wherein the solution comprises a potassium hydrogen phosphate.

* * * * *